(12) United States Patent
Bartl et al.

(10) Patent No.: US 10,363,005 B2
(45) Date of Patent: Jul. 30, 2019

(54) METHOD AND X-RAY APPARATUS FOR INTERFEROMETRIC 2D X-RAY IMAGING (71) Applicant: SIEMENS HEALTHCARE GMBH, Erlangen (DE)

(72) Inventors: Peter Bartl, Erlangen (DE); Martino Leghissa, Wiesenthau (DE); Marcus Radicke, Veitsbronn (DE); Sven-Martin Sutter, Herzogenaurach (DE); Thomas Weber, Hausen (DE)

(73) Assignee: Siemens Healthcare GmbH, Erlangen (DE)

( * ) Notice: Subject to any disclaimer, the term of this patent is extended or adjusted under 35 U.S.C. 154(b) by 270 days.

(21) Appl. No.: 15/456,811

(22) Filed: Mar. 13, 2017

(65) Prior Publication Data

US 2017/0258423 A1    Sep. 14, 2017

(30) Foreign Application Priority Data

Mar. 11, 2016  (DE) .................. 10 2016 204 046

(51) Int. Cl.
 *G03H 5/00*  (2006.01)
 *A61B 6/00*  (2006.01)
(52) U.S. Cl.
 CPC .......... *A61B 6/4291* (2013.01); *A61B 6/4035* (2013.01); *A61B 6/484* (2013.01)
(58) Field of Classification Search
 CPC ......... A61B 6/4291; A61B 6/484; A61B 6/00; A61B 6/4007; A61B 6/508; A61B 6/4035; A61B 6/4092; A61B 6/4441; A61B 6/502; A61B 6/5205; A61B 6/5258; A61B 6/032; A61B 6/0435; A61B 6/06; A61B 6/027;

(Continued)

(56) References Cited

U.S. PATENT DOCUMENTS 8,855,265 B2 * 10/2014 Engel .................. A61B 6/00
                                                      378/36
9,453,803 B2    9/2016 Radicke
(Continued)

FOREIGN PATENT DOCUMENTS

DE    102013214393 A1    11/2014

OTHER PUBLICATIONS

Zanette, et al.; 'Interlaced phase stepping in phase-contrast x-ray tomography'; Applied Physics Letters; Feb. 28, 2011; 98(9), 094101; 2011.
Pfeiffer, et al.; "Phase retrieval and differential phase-contrast imaging with low-brilliance X-ray sources"; Nature Physics; vol. 2 Apr. 2006; pp. 258-261; doi: 10.1038/nphys265; 2006.
Pfeiffer, et al.; "Hard X-ray dark-field imaging using a grating interferometer"; Nature Materials, vol. 7, No. 2; 2008, pp. 134-137; ISSN:1476-1122; DOI: 10.1038/nmat2096; XP55003146;; 2008.

*Primary Examiner* — Irakli Kiknadze
(74) *Attorney, Agent, or Firm* — Laurence Greenberg; Werner Stemer; Ralph Locher (57) ABSTRACT

A method and an x-ray apparatus for interferometric 2D x-ray imaging, use a Talbot-Lau interferometer having at least one phase grating and an analysis grating for producing 2D images of an object to be examined using a phase stepping method. A stepwise readout of a detector is carried out continuously at a multiplicity of the phase positions of an interference pattern. Time sequences of readout interval data records which overlap in time are extracted from the readout data records, and at least one result image data record is calculated from an absorption image and/or a phase-contrast image and/or a dark-field image from each readout interval data record.

17 Claims, 4 Drawing Sheets

(58) Field of Classification Search
CPC ..... A61B 6/481; A61B 6/504; A61B 10/0233; A61B 6/04; A61B 6/0414; A61B 6/12; A61B 6/4085; A61B 6/466; A61B 6/505; A61B 6/4488; A61B 6/48; A61B 6/5282; A61B 6/586; G21K 2207/005; G21K 1/02; G21K 1/06; G01N 23/04; G01N 23/20075; G06T 2207/10116; G06T 11/005; G06T 2207/30008; G06T 2207/30168; G06T 7/0002; G06T 11/00; G06T 11/006
USPC .................................................... 378/36, 62
See application file for complete search history.

(56) References Cited

U.S. PATENT DOCUMENTS

| | | | |
|---|---|---|---|
| 2005/0286680 A1* | 12/2005 | Momose | A61B 6/06 378/62 |
| 2006/0094950 A1* | 5/2006 | Ning | A61B 6/032 600/407 |
| 2007/0183595 A1* | 8/2007 | Liu | H04N 7/186 380/201 |
| 2010/0220832 A1 | 9/2010 | Ning et al. | |

* cited by examiner

METHOD AND X-RAY APPARATUS FOR INTERFEROMETRIC 2D X-RAY IMAGING

CROSS-REFERENCE TO RELATED APPLICATION

This application claims the priority, under 35 U.S.C. § 119, of German application DE 10 2016 204 046.4, filed Mar. 11, 2016; the prior application is herewith incorporated by reference in its entirety.

BACKGROUND OF THE INVENTION

Field of the Invention

The invention relates to a method for interferometric 2D x-ray imaging, using a Talbot-Lau interferometer containing at least one phase grating and an analysis grating for producing 2D images of an object to be examined using a phase stepping method. Wherein an interference pattern with a period is respectively produced at intervals by the phase grating in accordance with the Lau condition. The interference pattern being read stepwise in succession at different phase positions with the aid of the analysis grating and a pixelated detector disposed downstream in the beam direction at at least three phase positions within at least one period of the interference pattern, in order to determine a result image data record from an absorption image and/or a phase-contrast image and/or a dark-field image.

Furthermore, the invention relates to an x-ray apparatus for the interferometric x-ray examination of an object to be examined, containing an interferometric emitter-detector arrangement having a beam path in which the object to be examined may be arranged. At least one phase grating is arranged in the beam path, by means of which phase grating a self-image of the phase grating is produced as an interference pattern at at least one distance. The interference pattern being read out with the aid of an analysis grating upstream of the detector in a phase-stepping mode. A computer system contains at least one program memory in which program code is stored. The program code being run during the operation of the x-ray apparatus.

Interferometric x-ray imaging is a variant of phase-contrast imaging and is based on the introduction of one, two or three gratings into the beam path of an image-detector arrangement of an x-ray imaging system. Typically, the gratings are referred to in sequence as $G_0$, $G_1$ and $G_2$ along the beam direction.

The first grating $G_0$ is an absorption grating and situated near the focus of the x-ray source in the beam path, and it is therefore also referred to as a source grating. In the case of a focus which cannot provide the required spatial coherence for the imaging, it ensures that the coherence condition which is important for the imaging is observed by virtue of producing a multiplicity of quasi-coherent individual rays. If the x-ray focus is very small, as occurs in the case of a micro-focus tube, the source grating $G_0$ is not required and may be omitted. The source grating $G_0$ is normally constructed as a linear grating such that the coherence condition is satisfied in one direction. However, it may also have a checkerboard-like structure and thus satisfy the required coherence in two directions. The distances between the grating lamellas are typically configured in such a way that the Lau effect is satisfied, and so there is constructive superposition of the individual cutouts of the in the image plane.

As a rule, the second grating $G_1$ is configured as a phase grating. The Talbot effect is used in the design, the effect, in relation to a selected x-ray energy or x-ray wavelength, producing a self-image of the grating at specific distances from the phase grating $G_1$ in the form of an interference pattern arising there. The self-image of the phase grating $G_1$ is interfered with by the introduction of an object to be examined into the beam path. The absorption, differential phase shift and dark-field image information items may be obtained from these interferences.

If a medical standard detector is used for scanning, the pixel resolution of the detector generally does not suffice for reading out the interference pattern. In this case, the introduction of a further analysis grating $G_2$ becomes necessary. This grating is matched in terms of grating period to the undisturbed self-image of the grating $G_1$.

By displacing one of the gratings situated in the beam path—the analysis grating $G_2$ is typically used to this end—and by reading the detector without an object to be examined and with an object to be examined, it is possible to obtain absorption, differential phase shift and dark-field image information items. The displacement of the grating is referred to as phase stepping in the literature. By way of example, reference is made to the article F. Pfeiffer et al., "Hard X-ray Dark-Field Imaging Using a Grating Interferometer", Nature Materials 7 (2008).

By evaluating the obtained image information items, it is possible to produce two-dimensional representations of an object to be examined; the latter may be used in the generally known manner for diagnosing a patient.

A substantial problem of such a production of image data for diagnostic purposes consists of the fact that, for producing a final result image, all required measurements running in the phase stepping mode, that is to say at least 3 measurements, but in practice more likely to be 8 to 16 measurements, need to be complete in order to be able to display a result image. Since the duration of each measurement approximately corresponds to the duration of a conventional absorption measurement, the time required for creating a usable image representation also lengthens accordingly by a factor of at least 3, but more likely by a factor of 8 to 16 in practice. Expressed differently, the image rate of a recording sequence reduces by at least ⅓, or at least by ⅛ to 1/16 in practice.

SUMMARY OF THE INVENTION

It is therefore an object of the invention to find a method and an x-ray apparatus which supply faster image results, in particular which facilitate a current fluoroscopy of a patient.

This object is achieved by the features of the independent patent claims. Advantageous developments of the invention are the subject matter of the dependent claims.

The inventors have identified that the phase stepping may be carried out in an endless loop in the case of a fluoroscopy sequence or video recording sequence. Here, the measurements carried out in a stepwise fashion, respectively with a shifted grating (phase steps), for example the measurements m to n, are used for reconstructing an image data record. Here, the variables m and n with $n>=m+3$ should represent a continuous numbering of measurements made successively in time at the times $t_i$ with $i=1$ to m or $i=3$ to n. The next image data set ascertained according to the invention then obtains the phase steps m+1 to n+1 as input data. Using this, an image rate is produced which equals the recording rate of the phase-step recordings. Here, temporal averaging of the image information is present over the interval $t_n$ to $t_m$.

Unlike what was conventional until now, what may be achieved thus is that, once a result image created by at least three phase step measurements is obtained, it is no longer necessary to wait for at least three phase-steps measurements to be carried out once again in order to obtain a new result image. Instead, the previous set of measurement data is used once again, wherein at least one oldest phase step measurement is deleted and the same number of new phase step measurements is appended temporally at the front or, from a numbering point of view, at the back. As a result, the image rate for the x-ray recording according to the invention may be raised up to the image rate of the phase stepping. Previously, an image set is only shown after phase stepping was carried out in its entirety. In principle, the problem of temporal blurring over the phase steps, i.e. the entire data acquisition time period, used for the result image representation also exists in image representations generated thus. However, this does not represent deterioration in relation to the prior art.

Additionally, weighting of the phase steps in the reconstruction may be carried out, wherein, preferably, the weighting of the measurement values in the reconstruction algorithm of the result image may be undertaken for the absorption, the phase and the dark field by way of a functional relationship with time. Preferably, the weighting can become ever weaker, the further back in time the phase step lies. Moreover, intermediate image data records may be produced in each case from a plurality of subsets of the phase step measurements used overall, for example a 12-item series of 4 intermediate image data records from 3 phase step measurements in each case. Then, these intermediate image data records may be combined with different weightings to form the result image data record.

Furthermore, if more than three phase step measurements are available for producing a result image data record or respectively an intermediate image data record, it is also possible to eliminate invalid recordings from the overdetermined system of the image data production by way of plausibility considerations or trigger signals. By way of example, a particularly high deviation of the measurement data from the remainder, possibly pixel-by-pixel, of the image data or the average value thereof may count as a plausibility condition. A technical fault, for example of the x-ray tube, of the detector or of the phase-stepping apparatus, occurring in the x-ray system may be used as a trigger signal.

By way of the method according to the invention, it is now possible to carry out phase-contrast imaging or dark-field imaging in a fluoroscopy mode. To all practical intents, this may occur in "real-time" if the reconstruction is carried out parallel to the image acquisition. A time offset or a temporal inaccuracy of the representation is merely given by the period of time required for recording the phase-step measurements to be reconstructed.

Since the phase stepping cannot be continued endlessly continuously in one direction for mechanical reasons, the method described herein may be realized in different manifestations. Firstly, the grating position may be reset to the original start value when an end position of the phase stepping is reached and phase stepping may be started again from the start value. Secondly, the phase-stepping direction of the gratings may be reversed when an end position of the phase stepping is reached and the grating positions, as it were, can be passed over again in reverse.

It is possible to use three different methods of phase stepping in respect of the phase-stepping method carried out in the method according to the invention.

In a first embodiment—"step and shoot" method—the grating positions are approached in stepwise fashion and the acquisition of a phase step readout data record is carried out when the grating position has been stably reached. This corresponds to the method which is currently usually used in the literature.

In a second embodiment—"continuous phase stepping" method—the grating positions are continuously changed and phase step readout data records are acquired during the movement of the grating. This method requires a short exposure time of the detector and results in a high image rate. The advantage of this method lies in the fact that the phase stepping may be realized more easily from a mechanical point of view than a continuous movement or a continuously oscillating movement.

In a third embodiment—"electromagnetic phase stepping method"—the mechanically moved phase stepping is carried out by the controlled movement of the x-ray focal spot. To this end, it is possible to realize a closed trajectory of the focal spot track and hence of the phase stepping in endless loops.

According to the basic ideas described above, the inventors propose a method for interferometric 2D x-ray imaging, using a Talbot-Lau interferometer containing at least one phase grating and an analysis grating for producing 2D images of an object to be examined using a phase stepping method wherein an interference pattern with a period is respectively produced at intervals by the phase grating in accordance with the Lau condition. The interference pattern is read in temporal succession as readout data with the aid of the analysis grating and a pixelated detector disposed downstream in the beam direction at at least three phase positions within at least one period of the interference pattern, and a readout data record $A(t_i)$ is produced from the readout data (a) for each readout time $(t_1)$ and phase position $(p_i \sim t_i)$ and a readout interval data record $(AI(t_i-t_{i+7}))$ is produced within a time interval $(t_i-t_{i+7})$.

According to the invention, the method is improved by virtue of the fact that:
a) the stepwise readout of the detector is carried out continuously at a multiplicity of the phase positions of the interference pattern,
b) time sequences of readout interval data records which overlap in time are extracted from the readout data records, and
c) at least one result image data record is calculated from an absorption image and/or a phase-contrast image and/or a dark-field image from each readout interval data record.

Hence, the frame rate of the representation of the result image data record may be increased up to the step sequence of the phase stepping as a result of the fact that it is no longer the case that all readout data records required for the result image are produced anew but that earlier and already available readout data records are resorted to and only some of the older readout data records are replaced by new readout data records for producing a new readout interval data record. The new readout data records having the same size as the replaced readout data records. Here, the respective result image data record is calculated from the respectively current readout interval data record. The achieved frame rate changes depending on how many readout cycles or readout interval data records are awaited until the new production of the result image data records. At best, the frame rate may be matched to the rate of the phase stepping, wherein the required computational capacity accordingly increases with increasing frame rate or, vice versa, reduces therewith. As a result, there may also be a problem-free adaptation of the method according to the invention to the respectively available computing capacity or the computing capacity provided in the system if the calculation should take place in real time.

Accordingly, it is also proposed that a new readout interval data record is produced successively with each n-th production of a new readout data record with n>=1 from the new readout data record and at least two readout data records lying in the past and a new result image data record is produced therefrom.

An advantageous embodiment of the method therefore also provides for an image sequence of result image data records, i.e. a video, to be produced and, preferably, output, wherein each result image data record is formed from the same number of readout data records which on average shift in time.

Furthermore, the employed readout data records may be used with different weighting when producing the result image data records, wherein, particularly preferably, the readout data records which are further away in time from the reference time are weighted less strongly than readout data records which are closer to the reference time when weighting the readout data records, with the reference time changing for each result image data record. Thus, initially, unweighted ascertained readout data records are used which, in the manner described above, migrate successively to the front in time and these are then each weighted with a weighting function for the purposes of calculating the result image data record, the weighting function only orienting itself on the respectively used readout data records.

It may also be advantageous if, for the purposes of producing a final result image data record in each case, a plurality of intermediate image data records are initially produced from at least three readout data records lying in the past in each case and these intermediate image data records are combined with weighting to form a final result image data record.

Further advantageously, the intermediate image data records which are further away in time from a further reference time may be weighted less strongly than intermediate image data records lying closer to the further reference time when weighting the intermediate image data records.

Accordingly, m=k*n readout data records may be used for producing the final result image data record, preferably with m=12, n=3 and k=4. In so doing, k intermediate image data records from in each case n readout data records adjacent in time may also be calculated with the m readout data records and one final result image data record may be combined from the k intermediate image data records.

Moreover, the inventors propose that there is a sawtooth-like relative movement with multiple forward steps and one backward step during the spatially stepwise readout of the detector data, i.e. the phase-stepping method.

Furthermore, there may also be a cyclical relative movement with multiple forward steps and multiple backward steps during the spatially stepwise readout of the detector data.

Moreover, a relative movement of one of the x-ray gratings or of the object to be examined or of at least one focal spot in the emitter may be carried out for the spatially stepwise readout of the detector data.

The readout of the detector data may take place, firstly, during a standstill of the relative movement or, secondly, during part of the cyclical relative movement. This means that a continuous relative movement occurs in the latter case.

In addition to the method according to the invention described here, the inventors also propose an x-ray apparatus for the interferometric x-ray examination of an object to be examined, in particular of a patient. The apparatus contains an interferometric emitter-detector arrangement having a beam path in which the object to be examined may be arranged. At least one phase grating is arranged in the beam path, by which phase grating a self-image of the phase grating is produced as an interference pattern at at least one distance. The interference pattern being read out with the aid of an analysis grating upstream of the detector in a phase-stepping mode. The apparatus further having a computer system containing at least one program memory in which program code is stored, the program code being run during the operation of the x-ray apparatus. The program code which executes the method as claimed in one of the preceding method claims during the operation is also stored.

Advantageously, such an x-ray apparatus also contains a source grating which, in the beam direction, is arranged downstream of the emitter in the beam path.

Other features which are considered as characteristic for the invention are set forth in the appended claims.

Although the invention is illustrated and described herein as embodied in a method and an x-ray apparatus for interferometric 2D x-ray imaging, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Below, the invention is described in more detail with the aid of the figures, with only the features required for understanding the invention being depicted. Here, the following reference signs are used: 1: emitter-detector arrangement; 2: phase-stepping apparatus; 3: control element; 4: control and computation unit; I-V: method steps; $A(t_i)$: readout data record of the detector at the time $t_i$; $AI(t_i, t_{i+7})$: readout interval data record of the detector during the time interval $t_i$ to $t_{i+7}$; $A(t_i)$: readout data of the detector elements at the time $t_i$; D: x-ray detector; d: detector elements; F: focus; $G_0$: source grating; $G_1$: phase grating; $G_2$: analysis grating; $I_p$: radiation intensity at a detector element; M: interference pattern; m: measurement value; n: measurement value; O: object to be examined; S: x-ray beam; and $t_i$: measurement time.

Figure 1:
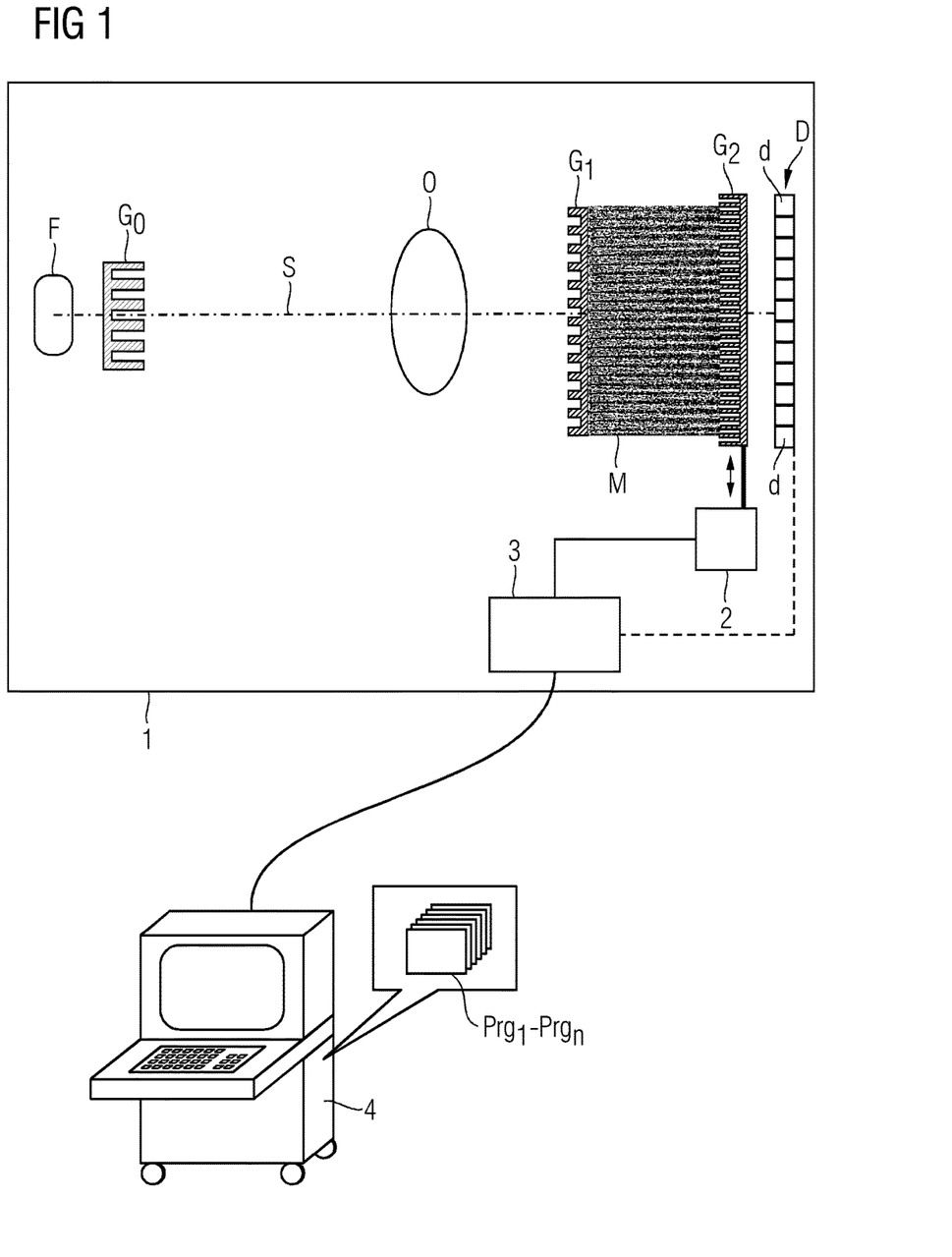
FIG. 1 is a schematic illustration of an x-ray system according to the invention.

Referring now to the figures of the drawings in detail and first, particularly to FIG. 1 thereof, there is shown a schematic illustration of an exemplary x-ray apparatus according to the invention, containing an emitter-detector arrangement which has a Talbot-Lau grating arrangement.

The emitter-detector apparatus 1 according to the invention contains a focus F as an emitter and a detector D which is pixelated into a multiplicity of detector elements, with a beam path forming therebetween. Directly behind the focus F in this beam path there is a source grating $G_0$ embodied as an absorption grating, the source grating producing quasi-coherent x-ray radiation in the form of a multiplicity of inherently coherent x-rays S. This is followed by a phase grating $G_1$ which produces an interference pattern M which produces a self-image of the phase grating at predetermined distances. With the aid of the subsequent analysis grating $G_2$, an interference pattern M may be read out pixel-by-pixel at the detector elements E in a phase-stepping mode with the aid of the phase-stepping apparatus 2, which displaces the analysis grating $G_2$ step-by-step during the measurement, and the following detector D.

The phase-stepping apparatus 2 is controlled by a control segment 3. This control segment 3 may also constitute part of the control and computational unit 4 which, otherwise, operates the control of the x-ray system and, where necessary, also carries out image reconstructions on the basis of measured projections. Overall, computer programs $Prg_1$-$Prg_n$ are stored in a memory of the control and computational unit 4, the computer programs being carried out during operation, for the purposes of carrying out at least the method steps according to the invention and also the mode of operation, known per se, of an interferometric x-ray apparatus.

The grating arrangement shown here, in which only the analysis grating $G_2$ is moved for the phase stepping, merely represents one example of an embodiment variant. The present invention may also be carried out in combination with phase-stepping methods in which one of the other x-ray gratings is used for the phase stepping. Alternatively, the focus or the focal spot on an anode of an x-ray tube may be moved in place of the grating, or an entire focal spot pattern on an anode of an x-ray tube may be displaced.

Figure 2:
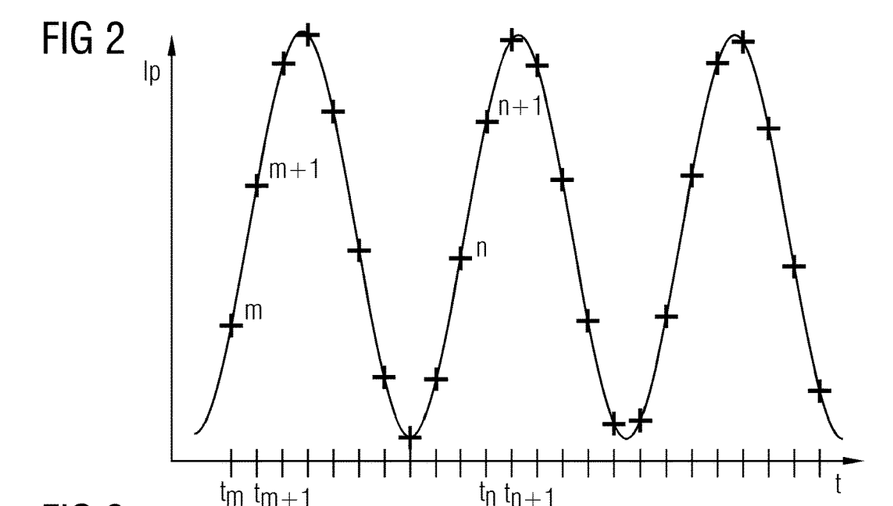
FIG. 2 is a graph showing a symbolized illustration of the timing of a conventional phase-stepping method on a basis of radiation intensity curve at a detector element.

FIG. 2 shows a schematic illustration of the intensity curve of an exemplary detector element E of the detector D in the case of a step-by-step readout of the radiation intensity Ip during a phase-stepping method downstream of an analysis grating $G_2$, which is displaced in a relative manner, of the apparatus from FIG. 1. The ordinate plots the measured radiation intensity Ip of a detector element or of the pixel formed thereby, while the abscissa forms the time axis t. Since the relative movement advances in time, each time position $t_i$ also represents a corresponding phase position $p_i$ in the interference pattern M. The measurement points from two conventional measurement data records of the phase-contrast measurement are denoted by m, m+1, . . . and n, n+1, . . . .

Figure 3:
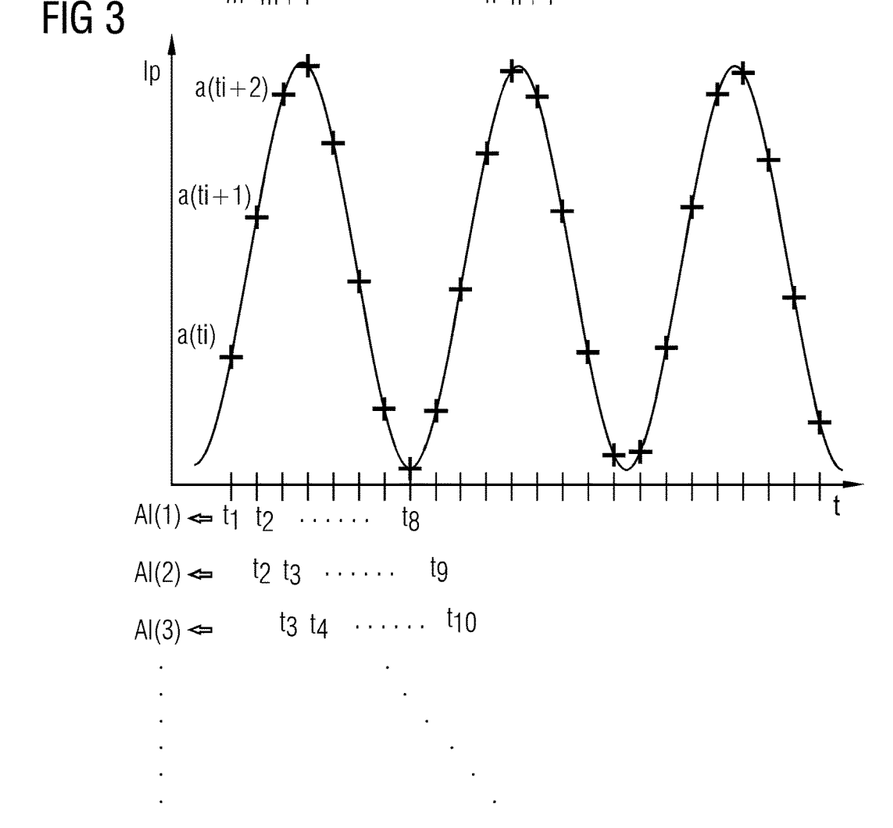
FIG. 3 is a graph showing a symbolized illustration of the timing of the first method according to the invention on the basis of the radiation intensity curve at a detector element with a frame rate equal to the phase stepping.

However, according to the invention, the measurements and calculations resulting therefrom are carried out using result image data records, as depicted in an exemplary manner in FIG. 3. Like FIG. 2, it shows the intensity curve Ip of a detector element or of a pixel resulting therefrom over the time t, with individual measurement points $a(t_i)$ being denoted by the "+" sign. In summary, the sum of the read measurement values $a(t_i)$ of all detector elements of a detector at the time $t_i$ forms a readout data record $A(t_i)$. At least three readout data records $A(t_i)$ are required at at least three phase positions $p_i$ within a time interval for the purposes of calculating a result image data record E(t). In the shown example, such readout interval data records AI(j) are formed over the time intervals $t_1$-$t_8$, $t_2$-$t_9$, etc. from the available readout data records $A(t_i)$ at the relevant measurement times and are depicted in a symbolized manner along the abscissa or time axis. Thus, readout interval data records with intervals progressing in time are formed here by virtue of an oldest readout data record being removed and a newest, preferably just measured, readout data record being added to the interval in each case, this being carried out successively from the readout interval data record to readout interval data record. If result image data records are calculated from these readout interval data records in each case, this results in a frame rate which corresponds to the readout rate of the readout data records.

Figure 4:
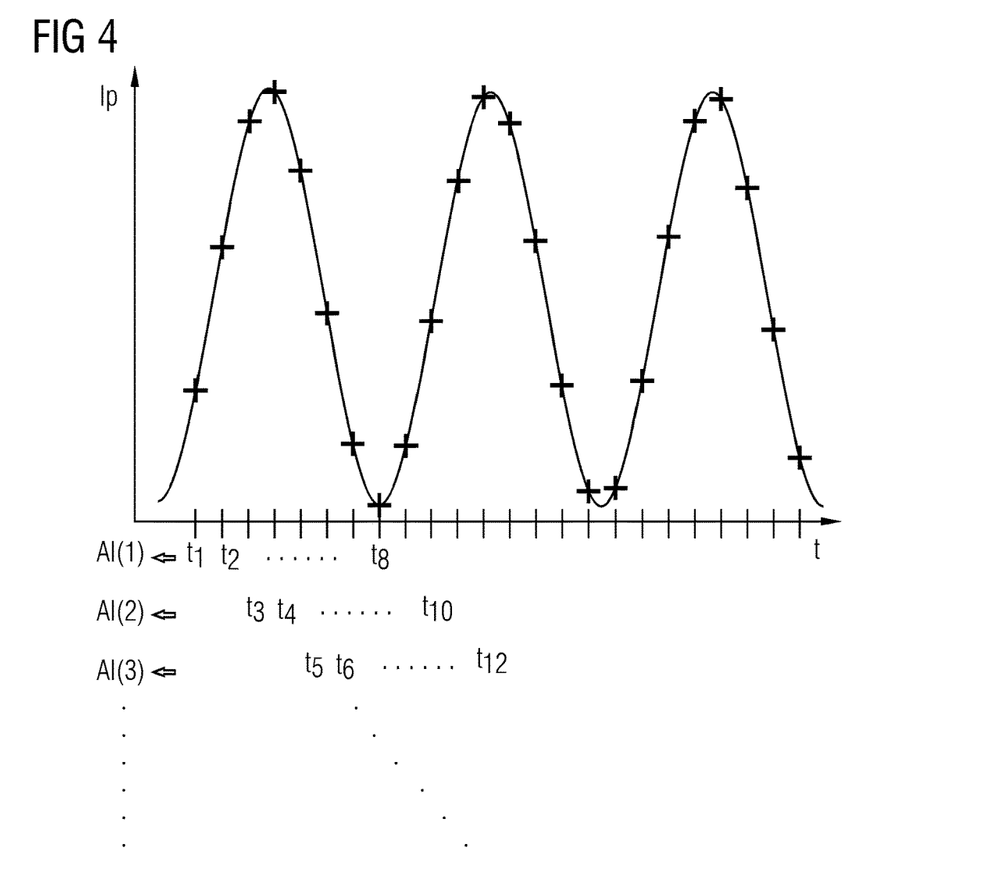
FIG. 4 is a graph showing a symbolized illustration according to FIG. 3, but with a frame rate which is half of that of the phase stepping.

FIG. 4 shows an illustration corresponding to FIG. 3, with, however, the difference from readout interval data record AI(j) to readout interval data record AI(j+1), etc. respectively being two measurement cycles or two readout data records. Accordingly, a frame rate which is only half as large emerges here.

Figure 5:
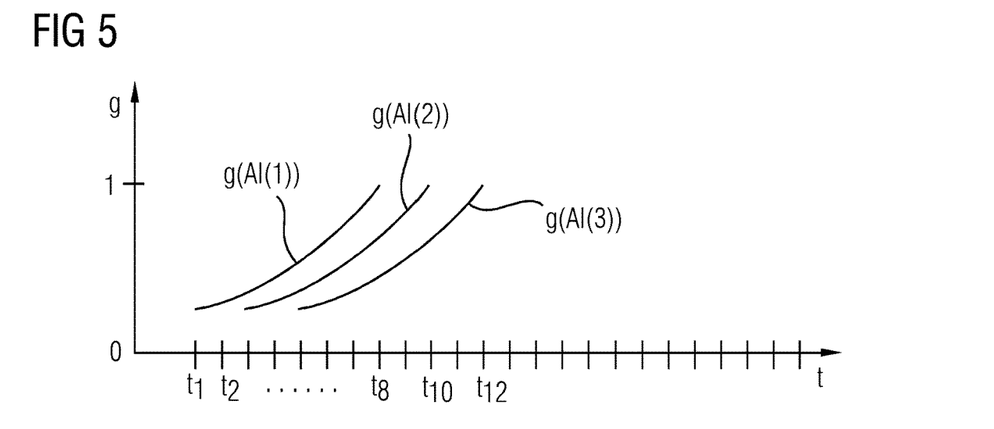
FIG. 5 is a graph showing an illustration of an exemplary weighting function for a continuous readout interval data records.

As already explained above, the produced and used readout data records may be used in a weighted manner when forming the calculation of the result image data record, with a reduction in the weighting with increasing temporal distance from the most current readout data record being preferred. FIG. 5 depicts such weighting curves g(AI(j)) in a manner fitting for the embodiment of the method according to FIG. 4 situated thereabove. Accordingly, each time interval obtains a dedicated weighting curve, with the weighting curve behaving relatively the same within the time intervals.

Figure 6:
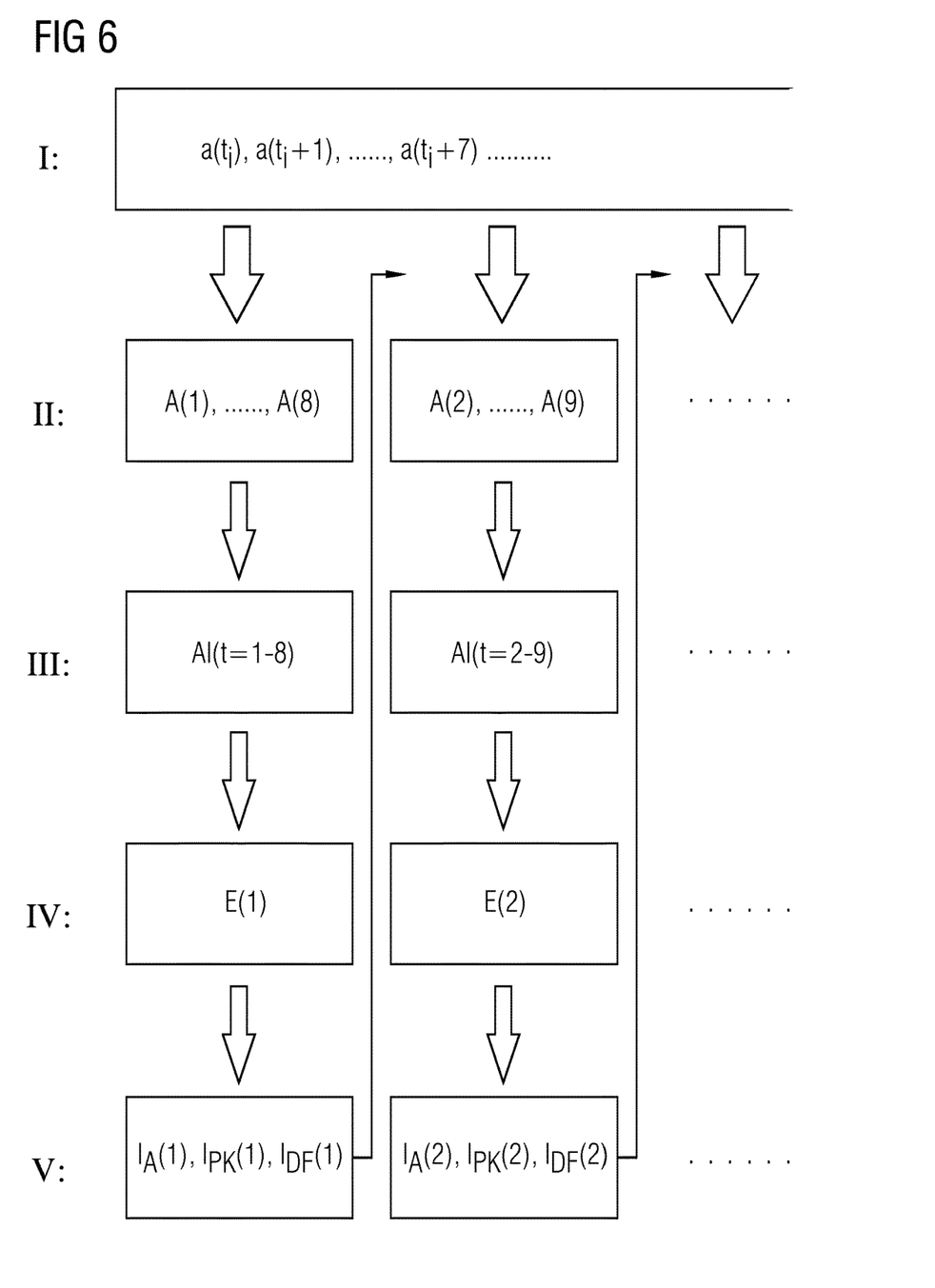
FIG. 6 is a flowchart showing the procedure of an exemplary method according to the invention.

Finally, FIG. 6 shows a flowchart for the procedure of an exemplary method according to the invention, without special weighting of the readout data. Here, the successive measurement of the readout data $a(t_i)$ is shown in step I. Reference is once again made here to the fact that, on account of the temporally advancing relative displacement of at least one of the x-ray gratings or of the focus with the change in time $t_i$, this is also accompanied by a shift of the interference pattern to advancing phase points $p_i$.

In the second step II, eight readout data records A(1) to A(8) at eight successive times (1) to (8) are respectively taken from the data pool of available readout data and, in step III, these are combined to a corresponding readout interval data record AI(t=1-8). A result image data record E(1) is calculated from this readout interval data record AI(t=1-8) in step IV, the result image data record containing at least one image data record containing the absorption $I_A(1)$, the phase-contrast $I_{PK}(1)$ or the dark-field information $I_{DF}(1)$. Accordingly, the corresponding image data records $I_A(1)$, $I_{PK}(1)$ and/or $I_{DF}(1)$ are output and/or stored in step V. Subsequently, there is a return to step II and steps II to V are carried out for a further time interval, in this case (2) to (9), wherein further readout data relating to at least one new time were ascertained previously, while carrying out steps II to V. If this procedure is carried out continuously, it facilitates a video representation of at least one of the result image data records in respect of the absorption, phase-contrast and/or dark-field with an image data rate corresponding at most to the readout rate of the detector.

Overall, the invention therefore proposes a method and x-ray device for interferometric 2D x-ray imaging, using a Talbot-Lau interferometer containing at least one phase grating and an analysis grating for producing 2D images of an object to be examined using a phase stepping method. The stepwise readout of the detector is carried out continuously at a multiplicity of the phase positions of the interference pattern, time sequences of readout interval data records which overlap in time are extracted from the readout data records, and at least one result image data record is calculated from an absorption image and/or a phase-contrast image and/or a dark-field image from each readout interval data record. Optional complementary features are described in detail above.

Even though the invention was illustrated more closely and described in detail by the preferred exemplary embodiment, the invention is not restricted by the disclosed examples and other variations may be derived herefrom by a person skilled in the art without departing from the scope of protection of the invention. In particular, the invention is not restricted to the feature combinations specified below, but other combinations and partial combinations which a person skilled in the art can obviously carry out may also be formed from the disclosed features.

The invention claimed is:

1. A method for interferometric 2D x-ray imaging with a Talbot-Lau interferometer, which comprises the steps of:
   using the Talbot-Lau interferometer having at least one phase grating and an analysis grating for producing 2D images of an object to be examined using a phase stepping method;
   producing an interference pattern with a period at intervals by the phase grating in accordance with a Lau condition, the interference pattern being read in temporal succession as readout data with an aid of the analysis grating and a pixelated detector disposed downstream in a beam direction at at least three phase positions within at least one period of the interference pattern;
   producing a readout data record from the readout data for each readout time and phase position and a readout interval data record is produced within a time interval;
   carrying out a stepwise readout of the pixelated detector continuously at a multiplicity of the phase positions of the interference pattern;
   extracting time sequences of readout interval data records which overlap in time from readout data records; and
   calculating at least one result image data record from at least one of an absorption image, a phase-contrast image or a dark-field image from each of the readout interval data records.

2. The method according to claim 1, which further comprises producing a new readout interval data record successively with each n-th production of a new readout data record with n>=1 from the new readout data record and at least two of the readout data records lying in a past and a new result image data record is produced therefrom.

3. The method according to claim 1, wherein an image sequence of result image data records is produced and, output, each of the result image data records is formed from a same number of the readout data records which on average shift in time.

4. The method according to claim 1, which further comprises using the readout data records with a different weighting when producing result image data records.

5. The method according to claim 4, wherein the readout data records) which are further away in time from a reference time are weighted less strongly than the readout data records which are closer to the reference time when weighting the readout data records, with the reference time changing for each of the result image data records.

6. The method according to claim 1, wherein for purposes of producing a final result image data record in each case, a plurality of intermediate image data records are initially produced from at least three of the readout data records lying in the past in each case and the intermediate image records are combined with weighting to form the final result image data record.

7. The method according to claim 6, which further comprises weighting the intermediate image data records which are further away in time from a further reference time less strongly than the intermediate image data records lying closer to the further reference time when weighting the intermediate image data records.

8. The method according to claim 7, which further comprises using m=k*n readout data records for producing the final result image data record).

9. The method according to claim 8, which further comprises calculating k said intermediate image data records from in each case n said readout data records adjacent in time with m said readout data records and the final result image data record is combined from the k intermediate image data records.

10. The method according to claim 8, which further comprises calculating k said intermediate image data records from in each case n said readout data records adjacent in time with m said readout data records and the final result image data record is combined from the k intermediate image data records, with m=12, n=3 and k=4.

11. The method according to claim 1, wherein there is a sawtooth-shaped relative movement with multiple forward steps and one backward step during the stepwise readout of detector data in the phase-stepping method.

12. The method according to claim 11, wherein the stepwise readout takes place during a standstill of a relative movement.

13. The method according to claim 11, wherein the step readout takes place during part of a cyclical relative movement.

14. The method according to claim 1, wherein there is a cyclical relative movement with multiple forward steps and multiple backward steps during the stepwise readout of detector data in the phase-stepping method.

15. The method according to claim 1, wherein there is a relative movement of one of the x-ray gratings or of the object to be examined or of at least one focal spot in an emitter during the stepwise readout of detector data.

16. An x-ray apparatus for an interferometric x-ray examination of an object to be examined, the x-ray apparatus comprising:
   an interferometric emitter-detector configuration having a beam path in which the object to be examined is disposed, said interferometric emitter-detector configuration having a detector, an analysis grating and at least one phase grating disposed in the beam path, and by means of said phase grating a self-image of said phase grating is produced as an interference pattern at at least one distance, the interference pattern being read out with an aid of said analysis grating disposed upstream of said detector in a phase-stepping mode; and
   a computer system having at least one non-transient program memory in which program code is stored, the program code being run during an operation of the x-ray apparatus, the program code executing the method according to claim 1 during the operation and is also stored.

17. The x-ray apparatus according to claim 16, wherein said interferometric emitter-detector configuration has an emitter; and
further comprising a source grating disposed downstream of said emitter.

* * * * *